United States Patent [19]

Nicolaou et al.

[11] 4,317,935

[45] Mar. 2, 1982

[54] BICYCLO ALDEHYDE AND PROCESS FOR PREPARATION

[75] Inventors: Kyriacos C. Nicolaou, Havertown, Pa.; Ronald L. Magolda, Vineland, N.J.; David A. Claremon, Philadelphia, Pa.

[73] Assignee: Research Corporation, New York, N.Y.

[21] Appl. No.: 194,399

[22] Filed: Oct. 6, 1980

Related U.S. Application Data

[62] Division of Ser. No. 87,678, Oct. 24, 1979, Pat. No. 4,260,806.

[51] Int. Cl.³ .................. C07C 47/44; C07C 45/27
[52] U.S. Cl. .................. 568/445; 568/820; 568/361; 568/665
[58] Field of Search ................................ 568/445

Primary Examiner—Bernard Helfin
Attorney, Agent, or Firm—Oblon, Fisher, McClelland & Maier

[57] ABSTRACT

Stable biologically active thromboxane $A_2$ analogues having the formula:

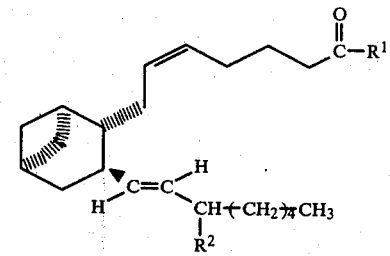

wherein
$R^1$ is $OR^3$, where $R^3$ represents hydrogen or a pharmaceutically acceptable cation or lower alkyl group; or
$R^1$ is $NR^4R^5$ where $R^4$ and $R^5$ are the same or different substituents selected from the group consisting of hydrogen and lower alkyl group; and
$R^2$ is hydrogen or an -OH group.

The thromboxane analogues are potent thrombotic agents, useful in cardiovascular treatment.

2 Claims, No Drawings

BICYCLO ALDEHYDE AND PROCESS FOR PREPARATION

This is a divisional of application Ser. No. 087,678, filed Oct. 24, 1979, now U.S. Pat. No. 4,260,806.

BACKGROUND OF THE INVENTION

1. Field of the Invention

This invention relates to stable, biologically active analogues of thromboxane $A_2$ useful as thrombotic agents.

2. Brief Description of the Prior Art

The prostaglandins were first discovered in the 1920's and have proven since then to be among the most ubiquitous pharmaceutically active compounds ever tested. Their use and the use of analogues and derivatives thereof, has been suggested in as wide a range of applications as fertility control, induction of labor, regulation of blood pressure, regulation of blood clotting, control of asthma, anticonvulsion, antidepressing action and many others. A new compound has recently been discovered (Nature 263, 663 (1976); *Prostaglandins*, vol. 12, 685 and 715 (1976); Chem. and Engineering News, Dec. 20, 1976) which belongs to the general family of prostaglandins. The compound has been named prostacyclin and its structure has been proven by synthesis (Johnson, et al, *Prostaglandins*, 12, 915 (1976); Corey et al, J. Amer. Chem. Soc., 99, 2006 (1977)) to be that of formula I. (The numbering system for prostacyclins is given for reference):

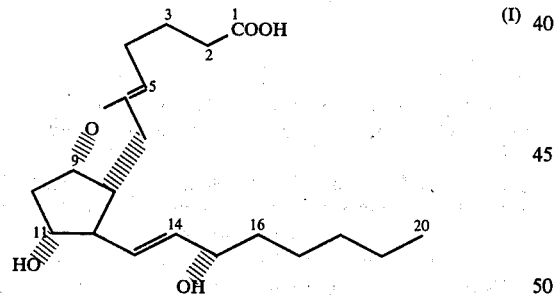

Its generic name is 6,9α-oxido-11α,15α-dihydroxyprosta (Z) 5, E (13)-dienoic acid. Prostacyclin is the most potent inhibitor of blood platelet aggregation of all the prostaglandins discovered to date. It has also been shown that prostacyclin destroys platelet aggregates after they have formed and that it has, in addition, a powerful action as a dilator of blood vessels. A second compound, which acts in an exactly opposite way to prostacyclin, has also recently been discovered by Hamberg and coworkers (Proc. Nat. Acad. of Sciences, USA, 72, 2994 (1975)). This metabolite, named thromboxane $A_2$ ($TA_2$) and shown in formula II below has potent thrombotic and smooth muscle constricting properties:

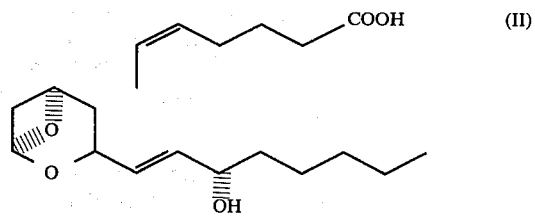

Both prostacyclin (I) and $TA_2$ (II) are derived from a common intermediate called endoperoxide, which in turn is synthesized from arachidonic acid by the enzyme cyclooxygenase. Prostacyclin is rapidly decomposed to 6-ketoprostaglandin $F_{1\alpha}$ (6-keto $PGF_{1\alpha}$) and $TA_2$ is rapidly decomposed by thromboxane $B_2$ ($TB_2$), less active final products in both cases. Both prostacyclin and $TA_2$ have very short half-lives under physiological conditions; that of prostacyclin being about 2 minutes and that of $TA_2$ only a mere 30 seconds at pH 7.4 and 37° C. The lability of $TA_2$ is caused by the presence of a sensitive bicyclic acetal system. The relationships between these metabolites, their precursors, products, and the enzymatic systems catalyzing their formations and decompositions, are summarized in Scheme I:

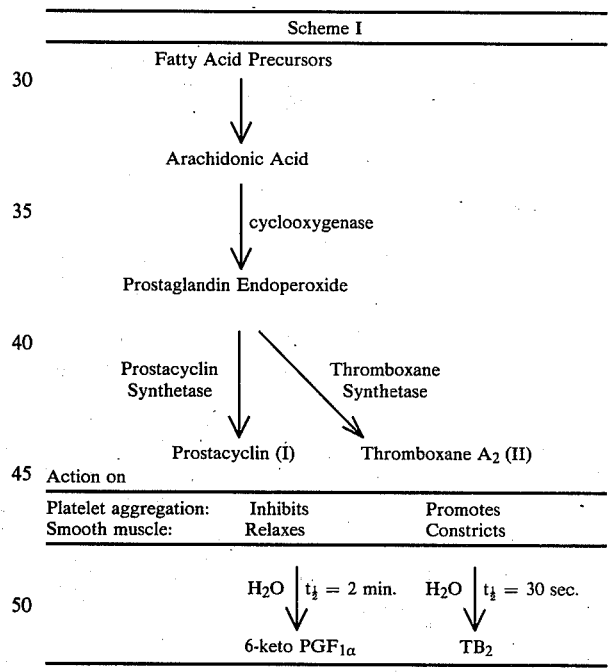

It can be seen that prostacyclin (produced by vascular endothelium) and thromboxane $A_2$ (produced by platelets) have opposite physiological effects and are very short lived. The balance between the levels of prostacyclin and thromboxane $A_2$, appears to maintain a finely tuned equilibrium between blood platelet aggregation versus dissolution and arterial constriction versus dilation.

Other important physiological effects which are mediated by the opposite transient actions of prostacyclin and $TA_2$ are the maintenance of the normal integrity of vessel walls, limitation of thrombus formation, assistance in the formation of hemostatic plugs by diminished prostacyclin formation, blood pressure regulation, control of inflammation, prevention of gastric ulceration and other similar effects. The pharmacological use of these metabolites however, is severely hindered by their short half-lives, especially so in the case of $TA_2$. Externally provided $TA_2$ will fail to reach its target tissues intact in high enough concentrations to cause any effects. Furthermore, the need to maintain the drug in a totally anhydrous condition also prevents its ready shipment, storage and testing for pharmacological applications. Therefore, if an analogue or derivative of $TA_2$ can be found which is stable and shows biological effects on blood platelets and arteries, such analogue would have wide applications in pharmacology and the treatment of cardiovascular and related diseases. The use of such a stable analogue of $TA_2$ can be used for patients with cardiovascular diseases, such as thrombosis, heart attack, or arteriosclerosis. It can be used in shock, such as hemorrhagic shock.

Although several stable bioactive prostacyclin analogues have been prepared (see, e.g., Nicolaou et al, Angewandte Chemie, Int. Ed. (English) 17, 293 (1978) and references cited therein; also U.S. patent application Ser. No. 886,141, filed Mar. 13, 1978) there have been, prior to this invention, only few reports of stable $TA_2$ analogues with biological activity.

Nicolaou et al, (Proceed. of Nat. Acad. Sci. USA, 76, 2566 (1979)) describe pinane thromboxane $PTA_2$ (formula III):

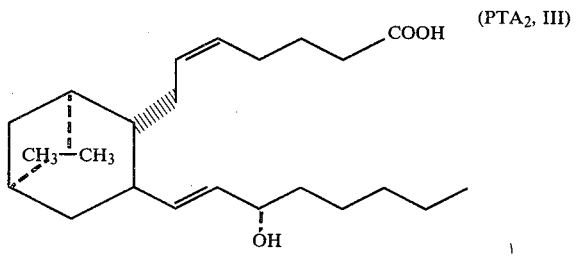

This compound is a stable, biologically active thromboxane $A_2$ analogue which inhibits coronary artery contraction at normal and high concentrations. It functions as an antagonist of natural $TA_2$. This compound ($PTA_2$) as well as a variety of derivatives and analogues thereof are disclosed in copending U.S. application Ser. No. 19,932, filed Mar. 12, 1979 by K. C. Nicolaou and R. Magolda. The synthesis of $PTA_2$ has also been disclosed by Ansell et al at the Fourth International Prostaglandin Meeting held in Washington, D.C., May 1979 (Abstracts of the Meeting, page 5). However, $PTA_2$ is the only stable $TA_2$ analogue reported to date. A need therefore continues to exist for other stable thromboxane $A_2$ analogues which show biological activity and are useful in cardiovascular therapy.

SUMMARY OF THE INVENTION

It is therefore an object of this invention to provide a thrombotic agent.

Another object of the invention is to provide a compound with vasoconstricting properties.

Still another object of the invention is to provide a stable biologically active analogue of thromboxane $A_2$.

A further object of the invention is to provide a stable biologically active analogue of thromboxane $A_2$ wherein the labile cyclic acetal linkages have been replaced by carbon atoms. Yet a further object of the invention is to provide a method for the synthesis of a stable biologically active analogue of thromboxane $A_2$.

Briefly, these and other objects of the invention which will hereinafter become more readily apparent, have been achieved by providing pharmaceutically active, stable analogues of thromboxane $A_2$ having the formula (IV) (together with the numbering used in this application):

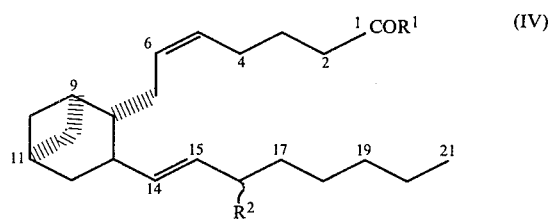

wherein $R^1$ is $OR^3$, where $R^3$ represents hydrogen or pharmaceutically acceptable cation or lower alkyl group; or $R^1$ is $NR^4R^5$, where $R^4$ and $R^5$ are the same or different and are selected from the group consisting of hydrogen and lower alkyl group;

and wherein $R^2$ is hydrogen or —OH.

DESCRIPTION OF THE PREFERRED EMBODIMENTS

The compounds of the present invention are stable pharmaceutically active thromboxane analogues of the formula (IV), shown below with a numbering system used in this application:

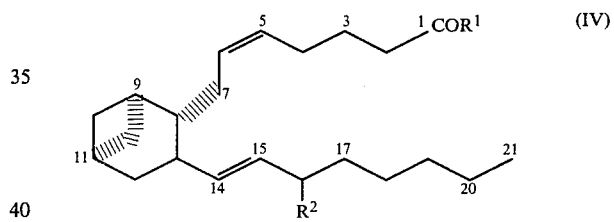

wherein $R^1$ is either $OR^3$, where $R^3$ represents hydrogen or a pharmaceutically acceptable cation or lower alkyl group; or $R^1$ is $NR^4R^5$, where $R^4$ and $R^5$ are the same or different and are selected from the group consisting of hydrogen and lower alkyl group; and wherein $R^2$ is hydrogen or S- or R-hydroxy group.

Pharmaceutically acceptable cations useful for the purposes of this invention are for example pharmaceutically acceptable metal cations or amine cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1, 3-propanediol, 2-amino-2-methyl-1-propanol, tris(hydroxymethyl)aminomethane, N-phenylethanolamine, N-(p-tertamylphenyl)diethanolamine, galactamine, N-methyl-glucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

Pharmaceutically acceptable lower alkyl groups are those derived from $C_1$-$C_{10}$ hydrocarbyl residues, especially $C_1$-$C_4$. Most preferred are methyl and ethyl groups.

When $R^2$=OH, two possible isomers at position 16 are possible (16R and 16S); the 16S isomer is preferred. The free acids($R^1$=OH), their esters ($R^1$=Oalkyl), salts ($R^1$=O-cation) and amides ($R^1$=N(Alkyl)$_2$ or NH$_2$ or NH(alkyl)) of the thromboxane analogues are all encompassed by the present invention. Specific compounds of the present invention are for example:
Compound IV wherein $R^1$=$R^2$=OH ($R^2$ is 16S).
Compound IV, wherein $R^1$=OLi, ONa, OK or OCs and $R^2$=OH (16S);
  wherein $R^1$=OCH$_3$ and $R^2$=OH (16S);
  wherein $R^1$=N(CH$_3$)$_2$ and $R^2$=OH (16S);
  wherein $R^1$=OH and $R^2$=H;
  wherein $R^1$=OCH$_3$ and $R^2$=H;
  wherein $R^1$=N(CH$_3$)$_2$ and $R^2$=H.

Gorman, R. et al, PNAS, USA 74, 4007 (1977) and Fitzpatrick, F. A., et al, Nature, 275, 764 (1978) have shown that prostaglandin endoperoxide (PGH$_2$) analogues which lack an —OH group at the 15 position are strong inhibitors of platelet aggregation. Thus for example 15-deoxy-9, 11-azo-PGH$_2$- a compound which contains an azo functionality bridging positions, 9,11-, inhibits platelet aggregation while the 15 —OH analogue has aggregating activity. 15-deoxy-9,11-epoxyimino-PGH$_2$, another stable PGH$_2$ analogue also inhibits platelet aggregation. Therefore, the thromboxane analogues of the present invention include in one of their preferred embodiments, compounds wherein $R^2$=H, as shown above for position 16.

The $C_1$-amide derivatives of prostaglandin PGF$_2$, have been shown to be antagonistic to the action of natural PGF$_2$, free acids by Ramwell, P. and his co-workers (Ramwell, P. et al, Nature, 278, 549 (1978)). Te use of the C-1 amides in the present invention is thus also one of the preferred embodiments.

The compounds of the present invention can be prepared from the bicyclic α,β unsaturated aldehyde V:

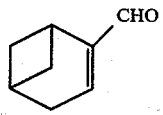  (V)

by a series of condensation and alkylation reactions, which are essentially analogous to those described in Nicolaou et al, Proc. Nat. Acad. of Sci., U.S.A., 76, 2566 (1979) and in Nicolaou and Magolda, co-pending U.S. application, Ser. No. 19,932, filed Mar. 12, 1979 and which is herein incorporated by reference. The aforementioned references disclose the synthesis of pinane thromboxane PTA$_2$ (III) from aldehyde VIa:

  VIa, R = —CHO
VIb, R = —CH$_2$OH

Aldehydes V and VIa differ in that VIa bears gem-dimethyl groups at bridge carbon 6 while V does not. In the aforementioned reference, aldehyde VIa was easily obtained by oxidation from the naturally occuring pinane alcohol (—)-myrtenol (formula VIb). There is however no naturally occuring—and thus readily available—bicyclic α,β unsaturated alcohol without a gem-dimethyl functionality at carbon 6 which can be used in the present case. The present inventors therefore had to develop a de novo complete synthesis of aldehyde VIa. In addition, to the best of Applicants' knowledge, aldehyde VIa has not been prepared before nor has a synthesis for it been suggested.

Aldehyde VIa can be prepared, according to this invention from bicyclo[3.1.1]heptan-2-one (formula VIIa):

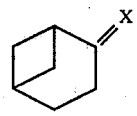  VIIa; X = O
VIIb; X = CH~O($C_1$-$C_4$ alkyl)

by treating VIIa with a reagent such as $C_1$-$C_4$ alkoxy methyl triphenyl phosphorane (($C_1$-$C_4$ alkyl)-O-CH=P(C$_6$H$_5$)$_3$), preferably methoxy methyl triphenyl phosphorane in a Wittig reaction, to yield the intermediate enol ether VIIb. The reaction is carried out in an excess of alkoxy methyl phosphorane, preferably about 2:1 excess, at low temperatures such as —20° to +10° C., in an inert solvent. A mixture of geometric isomers VIIb is obtained at the double bond. The enol ether VIIb (as the mixture) is then reacted with an aryl selenenyl halide such as phenyl selenenyl chloride, or bromide to give the selenenide VIII:

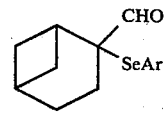  (VIII: Ar = aryl)

This reaction is carried out with a slight excess of the selenenyl halide reagent, preferably 1-1.5 equivalent excess, at very low temperatures, preferably —80° to 50° C. in an inert solvent such as a halohydrocarbon. It yields after work up and purification, selenenide VIII which is then transformed into target aldehyde (V) by oxidation with a 0-15% molar excess of an oxidation agent such as H$_2$O$_2$, m-chloroperbenzoic acid or the like, at —80° to 50° C. in an inert solvent, followed by treatment with base if needed to neutralize any acid present in the medium. The yield of aldehyde V from selenenide VIII is between 80 and 90% under these conditions.

The major problem of the synthesis is undoubtedly the construction of the strained bicyclo[3.1.1]heptane-2-one nucleus (VIIa). Although this ketone has been prepared in the prior art (Musso, H., et al, Chem. Ber., 100, 3614 (1967) and Gibson, T. J. Org. Chem., 37, 700 (1972)), the previous approaches are synthetically unattractive and proceed in low yields. The present inventors therefore investigated and developed two novel approaches to strained bicyclic ketone VIIa.

In the first approach, bicyclic[2.1.1]hexan-2-one (formula IX below) (prepared according to Bond, F. T., et al, Org. Phot. Syn. 1, 31 (1971)) was ring expanded by treatment with dibromomethane in base followed by a carbenoid-type rearrangement of the intermediate dibromoalcohol (X) with strong base. The sequence of reactions is shown in the following scheme:

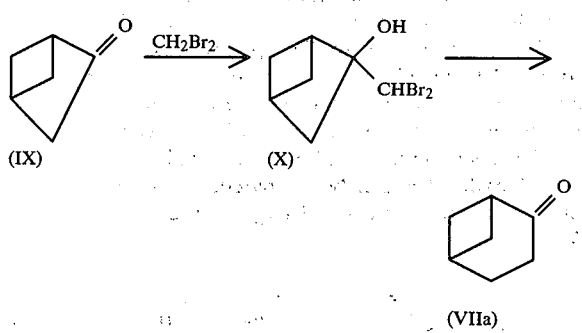

The preparation of dibromoalcohol X can be carried out according to Taguchi, H., et al, (J. Amer. Chem. Soc. 96, 3010 (1974)) by the addition of dibromomethane (2.1–2.5 equivalents) to a cold (−80° to −50° C.) solution (in an ether such as THF, diethyl ether, or the like) of IX in the presence of lithium diisopropyl amide (LDA)(1.5–2.5 equivalent). Dibromoalcohol X can be obtained in up to 95% yield. The ring expansion of X to VIIa can be carried out according to Taguchi et al, J. Amer. Chem. Soc., 96 6510 (1974). Treatment of the dibromoalcohol with an n-lower alkyl lithium, such as n-butyllithium, (2.0–2.5 equivalent excess) in an ether (diethyl ether, THF or the like), at low temperatures (−50° to −80° C.) generates a β-oxidocarbenoid species XI:

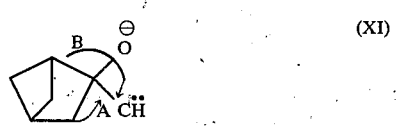

which undergoes bond rearrangement to the desired ketone VIIa (when bond a migrates) contaminated with bicyclo[3.1.1]heptan-3-one, the regioisomer of VIIa (when bond b migrates). The ratio of desired ketone VIIa to undesired regioisomer is about 6:1.

A second approach to ketone VIIa is more selective yet somewhat longer and involves the base-catalyzed cyclization of a ketone of formula XII in dilute solution at −10° to +40° C:

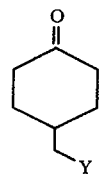

Y is a leaving group capable of being internally displaced by a base-generated α carbanion on said ketone of formula XII such as -acetyl, tosyl, trifluoroacetyl, trichloroacetyl, chloro, bromo, or the like. When an α-carbanion is generated in base on compound XII, the carbanion internally displaces the leaving group Y ($S_{Ni}$ reaction) yielding ketone VIIa. Preferably Y is tosyl and the internal displacement is carried out by 2.0–2.5 equivalents of dimsyl potassium (KH-DMSO) preferably 2.1 equivalents, in dilute DMSO solution at 15°–25° C. Ketone XII can be prepared from 1.4-cyclohexadione (commercially available from Aldrich Chemical Co.) by first protecting one of the two ketone groups of 1.4-cyclohexadione with an acid-sensitive protecting group (PG) such as diethylene glycol, then carrying out a Wittig-type condensation on the remaining, unprotected ketone group, with methyl triphenylphosphorane ($CH_2=P(C_6H_5)_3$) under standard, well-known Wittig reaction conditions. This two-step sequence yields compound XIII, wherein PG represents a standard ketone-protecting group (McOmie, Protecting groups in Organic Chemistry, Plenum Publishing, London, 1973).

The olefinic functionality of XIII is then hydrated at the primary carbon atom by the well-known borane/$H_2O_2$ reaction and, when Y is an acyl group, the resulting alcohol is finally acylated (with an anhydride or acid chloride, such as tosyl chloride or acetic anhydride for example) and its still protected ketone is deprotected under appropriate, well-known conditions (McOmie, Supra). Final yields of ketone XII are about 75% based on 1,4-dicyclohexanedione.

Having prepared the bicyclic α,β unsaturated aldehyde (V), all that remains of the synthesis is to carry this aldehyde to the final product carbocyclic thromboxane $A_2$ (formula IV). As mentioned supra, this can be done by following the detailed instructions in Nicolaou et al, copending U.S. application, Ser. No. 19,932, filed Mar. 12, 1979, which is herein incorporated by reference. Briefly, aldehyde V is treated in a Michael-type 1,4-addition with an unsaturated anionic alkyl to give trans-aldehyde XIV:

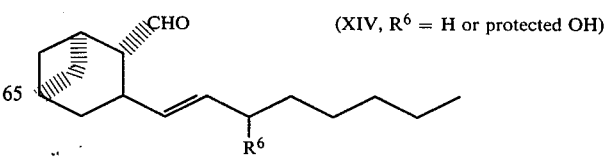

Aldehyde XIV is then reacted at the aldehyde group in a Wittig reaction with an lower alkoxy-methyl phosphorane followed by acid liberation of intermediate extended aldehyde XV

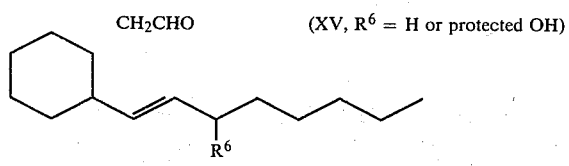

(XV, $R^6$ = H or protected OH)

Finally extended aldehyde XV is reacted with a carboxybutyl phosphorane, in a Wittig reaction, to yield, after esterification and/or amidation of the COO group and/or deprotection of the OH group, carbocyclic thromboxane IV. Preparation of the free acid or its corresponding salts can be carried by standard saponification methodology. When the 16-OH $CTA_2$ is prepared, two eprimers at C-16 are obtained.

The compounds of this invention can be administered by any appropriate means to warm-blooded animals. For example, administration can be parenterally, subcutaneously, intravenously, intramuscularly or intraperitoneally. Alternatively or concurrently, administration can be by the oral route. The dosage administered will be dependent upon the age, health and weight of the recipient, kind of concurrent treatment if any, frequency of treatment, and the nature of the effect desired. Generally, daily dosage of active ingredient compounds will be from about 0.5 mg to 50 mg per kg of body weight. Normally, from 1 to 30 mg per kg per day, in one or more applications per day is effective to obtain the desired result. The compounds can be employed in dosage forms such as tablets, capsules, powder packets, or liquid solutions, suspensions, or elixirs, for oral administration, or sterile liquid for formulations such as solutions or suspensions for parenteral use. In such compositions, the active ingredient will ordinarily always be present in an amount of at least 0.5% by weight based on the total weight of the composition and not more than 90% by weight.

Unlike thromboxane $A_2$ ($TA_2$), the carbocyclic thromboxane $A_2$ ($CTA_2$) of the present invention is stable at ambient temperatures in solution or heat. $CTA_2$ exhibits potent vasoconstricting (cat coronary arteries) properties with potencies comparable to those of the natural thromboxane $A_2$ yet possesses no intrinsic ability to agreggate platelets. $CTA_2$ also appears to be a potent inhibitor of arachidonic acid induced platelet aggregation. Nevertheless, $CTA_2$ induces sudden cardiac death in rabbits primarily by producing severe myocardial ischemia without coronary thrombosis.

Thus, in contrast to pinane thromboxane $A_2$ ($PTA_2$) which is a selective inhibitor of coronary artery constriction, platelet aggregation and thromboxane formation, the new analogue of this invention behaves partly as a biological mimic to thromboxane $A_2$. This is a truly surprising result since the only structural differences between $CTA_2$ and $PTA_2$ are in the absence and presence of a gem-dimethyl functionality at carbon C-6 of the molecules, respectively. That such diametrically opposite biological behavior would be obtained upon such relatively small structural change is quite unexpected. The thromboxane analogues of the present invention are useful in the treatment of thrombotic conditions, of blood clotting in heart attack cases, in artherosclerosis, diabetes and cerebral strokes. They are useful in the various types of shock, such as hemorrhagic shock.

Having generally described the invention, a more complete understanding can be obtained by reference to certain examples, which are included for purposes of illustration only and are not intended to be limiting unless otherwise specified.

I. Experimental Methods of Biological Testing

Thromboxane $A_2$ analogues (up to 4 μl of a 2.5 mM solution in ethanol) were tested for their effects on cat coronary arteries continuously perfused with 10 ml Krebs-Henseleit solution as described below.

Cats of either sex (2.5-3.5 kg) were anesthetized with sodium pentobarbital (30 mg/kg) given intravenously. Hearts were rapidly excised and placed in oxygenated (95% $O_2$+5% $CO_2$) ice-cold Krebs-Henseleit (K-H) solution of the following millimolar composition: NaCl, 118; KCl, 4.75; $CaCl_2$ $H_2O$, 2.54; $KH_2PO_4$, 1.19; $MgSO_4 7H_2O$, 1.19; $NaHCO_3$, 12.5; glucose, 10.00. A 20-gauge stainless steel cannula was inserted into the right coronary artery via the coronary ostium. Distal to the cannula, approximately 1 cm of coronary artery was dissected free of surrounding tissue. The section of right coronary artery with the cannula in place was excised from the heart and immediately transferred to a constant flow perfusion apparatus.

The perfusion apparatus consists of a reservoir containing 20 ml of warm (37° C.) oxygenated (95% $O_2$+5% $CO_2$) K-H solution which bathes the coronary artery and serves as recirculating perfusate. An increase in perfusion pressure signifies vasodilation. Following an initial 1 hr. equilibrium period, vascular responsiveness was established by adding 25 mM KCl. After washing with fresh K-H solution for 20-30 minutes, the preparation achieved a relatively constant low basal tone. Basal perfusion pressure averaged 50±2.5 mm Hg. Fresh K-H dilutions of stock thromboxane analog concentrations were added to the perfusate reservoir in 0.1-0.2 ml volumes. Changes in perfusion pressure in response to thromboxane analogue addition generally plateaus within 5 minutes of administration. Constriction of the arteries was induced by addition of 15 or 30 nM 9,11-azo-prostaglandinendoperoxide (azo-$PGH_2$), or 1 μM 9,11-methanoepoxy-$PGH_2$. These compounds and their effects are described in the following references: Corey et al, PNAS, USA 72, 3355 (1975); Bundy, G. L., Tetr. Lett, 1957 (1975); Malmsten, C., Life Sci, 18, 169 (1976) and Smith, J. B., et al, in Platelets and Thrombosis, Ed. by Mills, D.C.B. et al, Academic Press, London/N.Y. 1977, pp 83-95.

Platelet aggregation was studied in an aggregometer (Chronolog Corp., Phila., PA) using 0.5 ml citrated human platelet-rich plasma at 35° C. One minute after addition of analogue (up to 2 μl of a 25 mM solution in ethanol) aggregation was initiated by addition of sodium arachidonate (0.3-0.5 mM), ADP (2 μM) collagen (1 μg/ml), epinephrine (50 μM), 9,11-azo-$PGH_2$ (0.1-0.6 μM). The analogues were also tested for their effects on the inhibition of ADP-induced aggregation by 2 nM prostacyclin or 20 nM prostaglandin $D_2$.

To study the effect of $CTA_2$ on intact animals, New Zealand white rabbits 2-3.5 kg were anesthetized with pentobarbital sodium (25 mg/kg) and placed in the supine position. The right femoral and external jugular veins and the left common carotid artery were cannulated with polyethylene catheters. Standard limb needle electrodes were placed subcutaneously for recording the electrocardiogram (ECG). The trachea was cannulated with a glass connected to a pressure transducer for the recording of airway pressure. Mean arterial blood pressure (MABP), central venous pressure (CVP), airway pressure, and lead III of the ECG were continuously recorded on a Grass Model 7 oscillographic recorder. Sodium arachidonate (95% pure, Sigma Chamical) at 2.0 mg/kg or $CTA_2$ (125 µg/kg) were injected into the femoral arterial catheter, and the rabbit observed until death. Two ml blood samples were drawn into 25 mM EDTA just prior to injection of drug and just prior to death for radio-immunoassay of thromboxane $B_2$.

II. Chemical Results

1. Synthesis of Carbocyclic Thromboxane $A_2$ ($CTA_2$), Methyl Ester (IV) $R^1$=OH (16S and 16R configurations))

a. Preparation of Intermediate Bicyclo[3.1.1]heptan-2-one from Bicyclo[2.1.1]hexan-2one

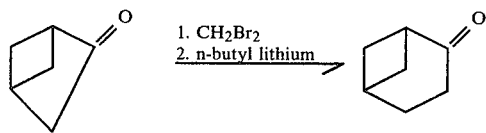

Bicyclo[2.1.1]hexan-2-one (Bond, F. T., et al, *Org. Phot. Syn.* 1, 31 (1971)) was ring expanded by a first addition of LDA (2.0 equiv) to a cold (−78° C.) solution of the bicyclo hexan-2-one in the presence of 2.2 equiv. of dibromoethane, followed by treatment of the resulting bromoalcohol intermediate with n-butyllithium (2.2 equiv) in ether at −78° C. to generate a 6:1 mixture of bicyclo[3.1.1]heptan-2-one (desired isomer) and bicyclo[3.1.1]heptan-3-one (undesired regioisomers) in 75% total yield. The analytical data for this compound agreed with published data from Musso, H, *Chem. Ber.*, 100, 3614 (1967) and Gibson, T., *J. Org. Chem.* 37, 700 (1972).

b. Preparation of Intermediate Bicyclo[3.1.1]heptan-2-one from 1,4-cyclohexadione

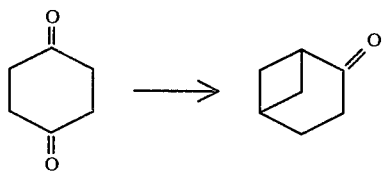

1,4-cyclohexadione (Aldrich) was treated with excess ethyleneglycol ($HOCH_2CH_2OH$) under acidic conditions in refluxing benzene followed by acetic acid/THF/$H_2O$ (3:2:2) treatment at 45° C. for 15 hours to give the monoprotected compound. A Wittig reaction on the unprotected ketone group was then carried out with $Ph_3P=CH_2$ in DMSO at 25° C. to give 68% overall yield of the olefin. This olefin was then reacted with disiamyl borane/NaOH/$H_2O_2$ (1:1:3) followed by tosylation of the resulting primary alcohol with tosylchloride/pyridine/−20° C. to give the protected tosylate, which was deprotected with AcOH-THF-$H_2O$ 2:1:1, 75° C., 2.5 hours, in 77% overall yield. The ketotosylate was then cyclized in 65% yield to bicylco[3.1.1]heptan-2-one with dimsylpotassium (KH-DMSO) (2-1 equivs.) in dilute DMSO solution of 15°-25° C.

c. Conversion of Bicyclo[3.1.1]heptan-2-one to 2-carboxaldehyde, bicyclo[3.1.1]hept-2-ene

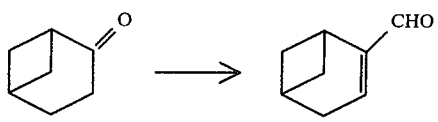

Treatment of bicyclo[3.1.1]heptane-2-one with methoxymethyl triphenylphosphorane (2 equiv) in THF/toluene at 0° C. afforded an enol ether at the 2-position as a mixture of E-and Z-isomers. The mixture was exposed to $C_6H_5$-Se-Cl (1.5 equivalents) in $CH_2Cl_2$ at −78° C. to produce, after aqueous work-up and chromatographic isolation an intermediate selenenide:

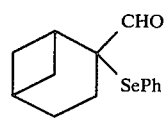

in 72% overall yield. Oxidation of the selenenide with m-CPBA (1.1 equiv) in $CH_2Cl_2$ at −78° C. followed by addition of diisopropyl amine (2.2 equiv) and warming to 25° C. resulted in the rapid formation of the desired title α,β-unsaturated aldehyde.

d. Preparation of Final Product from 2-carboxaldehyde-bicyclo[3.1.1]-hept-2-ene

The lower chain of the thromboxane molecule was introduced by 1,4-addition to the title α,β-unsaturated aldehyde, of the cuprate reagent obtained from (+)-trans-lithio-1-octen-3-ol tert-butyldimethylsilylether and 1-pentynylcopper hexamethylphosphoroustriamide complex (78% yield). The trans aldehyde ($J_{HaHb}$=10 Hz) was the major product of this reaction and was obtained exclusively as the thermodynamically more stable isomer (mixture of 16-epimers) after exposure to potassium carbonate in absolute methanol at 25° C. The upper side chain of the thromboxane was completed by (i) condensation of the trans-aldehyde with methoxymethylenetriphenylphosphorane (1.5 equiv) in toluene-THF solution at 0° C. furnishing an enol ether in 93% yield as a mixture of geometrical isomers (ii) quantitative liberation of the aldehyde from the enol ether by treatment with Hg(OAc)$_2$-kl in aqueous THF at 25° C. and (iii) Wittig reaction of the resulting extended aldehyde with the sodium salt of 4-carboxybutyltriphenylphosphorane in DMSO obtained as a mixture of diastereoisomers at the 16-position. After removal of the silyl ether (AcOH-THF-$H_2O$, 3:2:2, 45° C., 12h. 90 yield) the two diastereoisomers Rf=0.25 and Rf=0.28 (ratio ca 1:1) were separated chromatographically on silica gel plates using ethylacetate-petroleum ether mixtures (7.5:92.5) as solvent. The isomer with Rf 0.25- assumed to be the 16 S isomer on the basis of chromatographic mobility and biological activity, had the following analytical data:

$^1$H NMR (360 MHz, CDCl$_2$)τ: 4.43–4.75 (m, 4H, olefinic) 5.93 (m, 1H, CHO), 6.33, (3H, s, COOCH$_3$), 7.62–8.80 (m, 26H), 9.01 (t, J=9 Hz, 1H), 9.12 (t, J=5 Hz, 3H, CH$_3$); High resolution mass spec calc. for C$_{23}$H$_{38}$O$_3$: 362,2821 found: 362.2828; IR (CCl$_4$) νmax 3410 cm$^{-1}$ (OH), 1739 cm$^{-1}$ (COOCH$_3$).

Note: It is possible to prepare the optically active 16S isomer directly by starting with the optically active lithium/cuprate reagent, prepared form S-trans-lithio-1- octen-3-ol tert-butyldimethylsilyl ether and 1-pentynyl-copper hexamethylphophoroustriamide complex, instead of the (R,S-)-trans-lithio-1-octen-3-ol-tert butyldimethyl silyl ether.

2. Preparation of Carbocyclic Thromboxane $A_2$, free acid (IV, $R^1$=OH, $R^2$=—OH, 16S and 16R configurations)

Basic hydrolysis of the more polar compound obtained in Experiment 1 (Rf=0.25) in THF/LiOH solution at 25° C. led quantitatively to the 16S carbocyclic thromboxane $A_2$ analog whereas the less polar ester (Rf=0.28) after similar treatment afforded the 16R hydroxy epimer.

III. Biological Results

Carbocyclic thromboxane $A_2$ produced dose-dependent constriction (i.e., increased perfusion pressure at constant flow) in isolated perfused cat coronary arteries. $CTA_2$ was found to be more potent a constrictor than azo-$PGH_2$>9,11-methanoepoxy-$PGH_2$>9,11 epoxymethano-$PGH_2$>>$PGH_2$>>Thromboxane $B_2$. $CTA_2$ was 10,000 times as potent as $TB_2$ with regard to the concentration required to produce an increase in coronary perfusion pressure of 20 mm Hg ($EC_{20}$). $CTA_2$ was also 4 times as potent as 9,11-azo $PGH_2$ and 5-6 times as potent as the other two $PGH_2$ derivatives (i.e., 9,11-methanoepoxy $PGH_2$ and 9,11-epoxymethano $PGH_2$).

$CTA_2$ was a thromboxane agonist at all concentrations, and did not antagonize the coronary constrictor effects of 9,11-methanoepoxy $PGH_2$ even at concentrations up to $10^{-7}$ M. However, pinane thromboxane $A_2$, a thromboxane antagonist, almost completely antagonized the coronary constrictor effects of $CTA_2$. Thus, $CTA_2$ behaved as a pure thromboxane agonist on the coronary vasculature without any antagonist actions to endoperoxide-like analogs.

With regard to platelet aggregation, $CTA_2$ did not behave as a thromboxane agonist. It failed to induce platelet aggregation in vitro up to concentrations of 100 μM. Moreover, $CTA_2$ was a very potent inhibitor of platelet aggregation to a variety of prostanoids including arachidonic acid, 9-11-azo $PGH_2$, 9,11-methanoepoxy $PGH_2$ and 9,11-epoxymethano $PGH_2$. At 4 to 5 μM $CTA_2$ completely prevented induced platelet aggregation. However, lower concentrations (i.e., 1 to 4 μM) were only partially protective. In the case of arachidonic acid induced aggregation, lower concentrations of $CTA_2$ (i.e., 1-2 μM) delayed the onset of platelet aggregation without actually inhibiting the magnitude of the overall response, indicating an effect on the early phase of platelet aggregation.

The profile of $CTA_2$ appears to be unique amongst the thromboxane and endoperoxide analogs thus far reported. $CTA_2$ is a potent coronary vasoconstrictor, which does not antagonize the constrictor effects of endoperoxide analogs. It thus behaves as a potent thromboxane agonist on the vasculature. However, $CTA_2$ acts as though it is a thromboxane antagonist on platelet aggregation. It does not induce platelet aggregation itself, and it antagonizes the aggregatory action of arachidonic acid and endoperoxide analogs. Moreover, it selectively inhibits the formation of thromboxane $B_2$.

It was therefore of considerable interest to assess the overall effect of $CTA_2$ in the intact animal to determine whether its coronary vascoconstrictor effect or its inhibition of platelet activity predominated.

The typical response of an anesthetized rabbit to 125 μg/kg $CTA_2$ given intravenously is as follows: Within 1-2 min, arterial blood pressure started to decline, central venous pressure rapidly increased, and registration rate increased markedly but the depth of respiration became very shallow. Additionally, the ECG indicated myocardial ischemia; by six minutes, severe hypotension occurred, respiration became ineffective and ischemia became even more prominent; at nine minutes death ensued. Radioimmunoassay of blood samples from rabbits injected with 125 μg/kg $CTA_2$ revealed no increase in circulating $TB_2$ concentrations, values averaging 2.2±0.7 pmoles/ml prior to $CTA_2$ injection and 2.3±0.7 pmoles/ml just prior to death. On autopsy, no thrombosis or platelet aggregates could be detected in either the coronary or pulmonary bed, and this was verified by histological sections of the heart and lungs.

Having now fully described this invention it will be apparent to one of ordinary skill in the art that many changes and modifications can be made thereto without departing from the spirit or scope of the invention set forth herein.

What is claimed as new and intended to be covered by Letters Patent is:

1. An intermediate useful for the synthesis of carbocyclic thromboxane, having the formula:

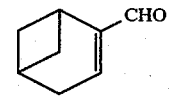

2. A method of preparing the intermediate of claim 1 which comprises reacting bicyclo[2.1.1]hexan-2-one of formula (1)

with 2.1-2.5 equivalents of dibromomethane, thereby obtaining dibromoalcohol of formula (2):

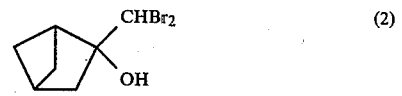

reacting dibromoalcohol (2) with 2.0-2.5 equivalents of a n-lower alkyl lithium, thereby to obtain bicyclo[3.1.1]hept-2-one, of formula (3):

reacting bicyclo[3.1.1]hept-2-one with about a 2:1 molar excess of a $C_1$-$C_4$ alkoxy methyl triphenylphosphorane to obtain an enol ether of formula (4):

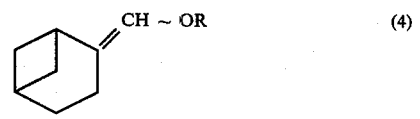

wherein R is $C_1$-$C_4$ alkyl group;
reacting said enol ether of formula (4) first with a 1.0-1.5 molar excess of an aryl selenenyl halide at $-80°$ to $-50°$ C., followed by oxidation with 0-15% excess of an agent selected from the group consisting of $H_2O_2$ and m-chloroperbenzoic acid, to thereby obtain the aldehyde of claim 1.

* * * * *

UNITED STATES PATENT AND TRADEMARK OFFICE
CERTIFICATE OF CORRECTION

PATENT NO. : 4,317,935

DATED : March 2, 1982

INVENTOR(S) : KYRIACOS C. NICOLAOU ET AL

Page 1 of 2

It is certified that error appears in the above—identified patent and that said Letters Patent is hereby corrected as shown below:

Column 2, lines 1-10, the formula should be amended to appear as follows:

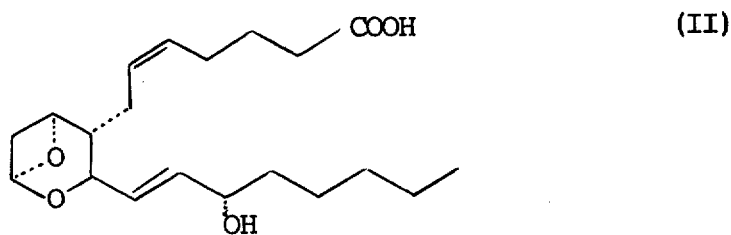

Column 3, lines 27-40, the formula should be amended to appear as follows:

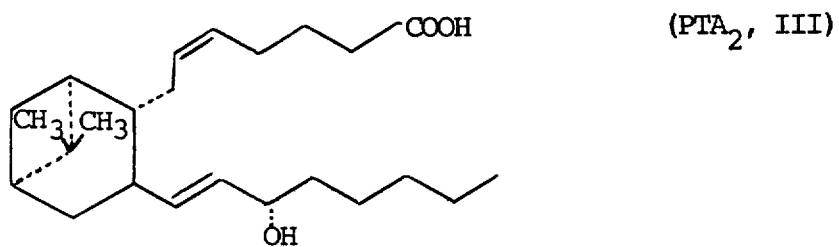

Column 5, line 56, delete "Te" and substitute therefor --The--.

Column 9, lines 5-11, the formula should be amended to appear as follows:

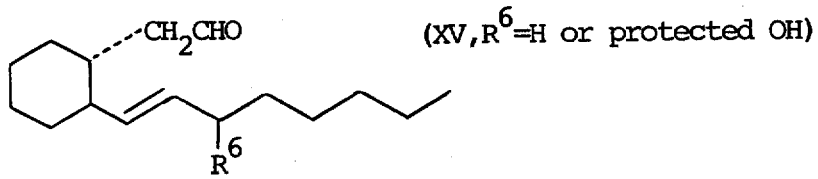

UNITED STATES PATENT AND TRADEMARK OFFICE
CERTIFICATE OF CORRECTION

PATENT NO. : 4,317,935

DATED : March 2, 1982

INVENTOR(S) : KYRIACOS C. NICOLAOU ET AL

It is certified that error appears in the above—identified patent and that said Letters Patent is hereby corrected as shown below:

Column 12, line 64, delete "362,2821" and substitute therefor --362.2821--.

Signed and Sealed this

Sixth Day of July 1982

[SEAL]

Attest:

Attesting Officer

GERALD J. MOSSINGHOFF

Commissioner of Patents and Trademarks